US008613376B2

(12) United States Patent
Gramann et al.

(10) Patent No.: US 8,613,376 B2
(45) Date of Patent: Dec. 24, 2013

(54) DEVICE FOR DISPENSING A DENTAL MATERIAL

(75) Inventors: Jens Gramann, Gräfelfing (DE); Ralf Kelz, Seefeld (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/392,946

(22) PCT Filed: Aug. 23, 2010

(86) PCT No.: PCT/US2010/046348
§ 371 (c)(1),
(2), (4) Date: May 14, 2012

(87) PCT Pub. No.: WO2011/025737
PCT Pub. Date: Mar. 3, 2011

(65) Prior Publication Data
US 2012/0231410 A1  Sep. 13, 2012

(30) Foreign Application Priority Data
Aug. 28, 2009  (GB) .................................. 0915008.7

(51) Int. Cl.
*B67D 1/00*  (2006.01)
(52) U.S. Cl.
USPC .......... 222/63; 222/137; 222/145.6; 222/333; 222/390; 433/198
(58) Field of Classification Search
USPC ............. 222/63, 137, 145.6, 145.1, 333, 386, 222/390, 392
See application file for complete search history.

(56) References Cited

U.S. PATENT DOCUMENTS

| 3,764,115 | A | * | 10/1973 | Buckingham et al. ........ 366/149 |
| 3,854,629 | A | | 12/1974 | Blieberger |
| 4,180,187 | A | * | 12/1979 | Ben-Haim .................... 222/326 |
| 4,181,825 | A | | 1/1980 | Epple |
| 4,693,397 | A | * | 9/1987 | Lang ............................. 222/137 |
| 4,878,601 | A | * | 11/1989 | Flemming et al. ............ 222/137 |
| 5,341,958 | A | | 8/1994 | Bayat et al. |
| 6,168,052 | B1 | * | 1/2001 | Keller .......................... 222/333 |

(Continued)

FOREIGN PATENT DOCUMENTS

| EP | 1 010 401 | 11/1998 |
| JP | 20077641 | 1/2007 |
| JP | 2007007641 | 1/2007 |
| WO | WO 2007/121003 | 10/2007 |

OTHER PUBLICATIONS

International Search Report for International Patent Application No. PCT/US2010/046348, dated Dec. 1, 2010.

*Primary Examiner* — Paul R Durand
*Assistant Examiner* — Randall Gruby

(57) ABSTRACT

A device for dispensing a dental material comprises a plunger for extruding a component of the dental material, and a motor for driving the plunger. The device has two electric circuits for powering the motor to drive the plunger forward or backward. A selector switch is arranged in the device for alternately selecting between the first electric circuit and the second electric circuit for powering the motor. The device further has switches for interrupting the first and/or second electric circuits when the plunger is positioned at certain positions. The device provides automatic functionality for facilitating dispensing of dental materials, and further is preferably relatively robust and relatively inexpensive to manufacture.

13 Claims, 11 Drawing Sheets

(56) References Cited

U.S. PATENT DOCUMENTS

| | | | |
|---|---|---|---|
| 6,311,871 B1 * | 11/2001 | Binder | 222/145.6 |
| 6,315,164 B1 | 11/2001 | Mühlbauer | |
| 6,572,259 B2 | 6/2003 | Burnett | |
| 6,837,612 B2 * | 1/2005 | Bublewitz et al. | 366/172.1 |
| 6,889,872 B2 * | 5/2005 | Herman et al. | 222/82 |
| 6,935,534 B2 * | 8/2005 | Strecker | 222/145.1 |
| 7,420,341 B2 * | 9/2008 | Glasgow et al. | 318/280 |
| 2002/0067147 A1 | 6/2002 | Glasgow | |
| 2002/0154568 A1 * | 10/2002 | Renfro | 366/169.1 |
| 2002/0154569 A1 | 10/2002 | Burnett | |
| 2003/0022128 A1 * | 1/2003 | Heymann et al. | 433/89 |
| 2007/0020580 A1 * | 1/2007 | Harre et al. | 433/89 |
| 2008/0267005 A1 * | 10/2008 | Reinprecht | 366/162.3 |
| 2009/0071986 A1 * | 3/2009 | Wang | 222/333 |
| 2009/0140007 A1 * | 6/2009 | Voss | 222/135 |
| 2010/0089949 A1 * | 4/2010 | Gramann et al. | 222/137 |
| 2010/0222921 A1 * | 9/2010 | Harre et al. | 700/239 |
| 2012/0148980 A1 * | 6/2012 | Gramann | 433/90 |
| 2012/0218856 A1 * | 8/2012 | Walter et al. | 366/307 |
| 2012/0292341 A1 * | 11/2012 | Gramann et al. | 222/137 |
| 2012/0295215 A1 * | 11/2012 | Jelovac et al. | 433/25 |

* cited by examiner

DEVICE FOR DISPENSING A DENTAL MATERIAL

CROSS REFERENCE TO RELATED APPLICATIONS

This application is a national stage filing under 35 U.S.C. 371 of PCT/US2010/046348, filed Aug. 23, 2010, which claims priority to Great Brittan Application No.0915008.7, filed Aug. 28, 2009, the disclosure of which is incorporated by reference in its/their entirety herein.

FIELD OF THE INVENTION

The invention relates to a device for dispensing a dental material, and in particular to a control circuitry for controlling the device.

BACKGROUND ART

For preparation of dental materials in a dental practice, dispensing devices are often used for automatically dispensing the materials from bulk containers. Such dispensing devices typically are used to prepare the materials in a relatively short time and at a desired quality. Further there are dispensing devices that allow automatic mixing of components to form the dental material.

For example EP 1 010 401 A1 discloses a device for providing a dental multi-component compound. The device has plungers for advancing components from cartridges into a mixer. Further the device has a unit for controlling a motor which drives the plungers at different speeds.

WO 2007/121003 discloses a dispenser which is adapted for advancing and mixing a dental material, comprising a drive which is operated on a non-uniform drive speed profile. An advancing speed profile may be provided for advancing the components and/or a mixing speed profile may be provided for mixing the components.

Although there is a variety of devices on the market which provide for automatic mixing and dispensing, there is still a desire to minimize costs for manufacturing of such devices and for providing the devices with maximized reliability.

SUMMARY OF THE INVENTION

The invention relates to a device for dispensing a dental material. The device comprises:
- a plunger for extruding at least a component of the dental material from a container;
- a first motor cooperating with the plunger;
- a first electric circuit which is adapted for powering the first motor to advance the plunger forward for extruding the material component;
- a second electric circuit which is adapted for powering the first motor to retract the plunger backward from the material;
- a selector switch which is adapted to alternately select the first electric circuit or the second electric circuit for powering the motor;
- a first switch which is arranged within the first electric circuit and being adapted to interrupt the first electric circuit when the plunger is positioned at a forward position; and
- a second switch which is arranged within the second electric circuit and being adapted to interrupt the second electric circuit when the plunger is positioned at a backward position.

In one embodiment of the device, the invention comprises at least two containers which preferably contain components of a dental material. The device may further be adapted to receive a preferably exchangeable mixer for mixing the components. Further the device may have a push button for operating the selector switch. Preferably the device can be used by operating the push button. For example, the push button may be activated (for example pressed) to start the device for dispensing material, and the push button may be released to stop dispensing. During dispensing, the plungers may displace to extrude the components from the container into the mixer where the components may be automatically mixed. The mixture may then be made available for use at an outlet of the mixer.

The invention is advantageous in that it may provide for a relatively robust and inexpensive dispensing device. In particular, the invention may allow minimizing the amount of electric and/or electronic components. Thus the reliability of the device may be maximized, but the manufacturing costs of the device may be minimized. Nevertheless the invention preferably allows making of a device that has adequate functionality for facilitating preparation of dental materials, for example in a dentist's practice. Certain embodiments of the device of the invention may even make the use of electronic components, like integrated circuits, unnecessary. The device according to the invention thus may be suitable for use under relatively rough environmental conditions. Therefore the device may for example be particularly suitable for use in mobile dental practices. The device may further be useable in areas where electric power undergoes relatively significant variations. Further the invention may allow maintenance, trouble shooting and/or repair works of the device to be facilitated, and for example may make the use of expensive test and/or measuring devices unnecessary.

In one embodiment the device is adapted such that the selector switch automatically resets to select the second electric circuit. The selector switch therefore preferably has at least two settings, a first setting in which the first electric circuit is selected or enabled, but the second electric circuit is disabled, and a second setting in which the second electric circuit is selected or enabled, but the first electric circuit is disabled. The selector switch may further have a third setting in which both the first and second electric circuits are disabled.

In another embodiment the selector switch is adapted to interrupt the second electric circuit along with or together with closing an interruption in the first electric circuit and thereby to select the first electric circuit. Further the selector switch is preferably adapted to interrupt the first electric circuit along with or together with closing an interruption in the second electric circuit and thereby to select the second electric circuit. Thereby the selector switch may allow for alternately selecting between the first and second electric circuits without selecting both electric circuits at the same time. Therefore short cuts during switching between the settings of the selector switch may be avoided.

In one embodiment the selector switch comprises a double pole double throw (DPDT) switch. The DPDT switch has preferably at least two double pole (DP) switches.

The skilled person will know many different embodiments for a DPDT switch. In one embodiment the DPDT switch resets automatically to a certain setting. Such a switch may for example comprise a mechanical switch which is urged by spring load toward a certain setting, but is manually movable toward an alternate setting. Therefore the selector switch may provide for automatically selecting a desired default mode of the device when not operated. This may make the operation of the device more convenient because a user does not need to manually operate the selector switch to activate the default mode.

In another embodiment the first and/or the second switch comprise(s) a mechanical switch. A mechanical switch may for example comprise a movable contact inside the switch which can be moved relative to a further contact to alternately establish or interrupt an electrical connection between the two contacts. The mechanical switch may be adapted such that the movable contact may be moved by mechanical connection to an actuator, by a magnet, or by moving (for example rotating) the switch, for example. The first and/or second switch(es) may in particular not comprise any capacitive, optical or acoustic switch. Further the first and/or second switch(es) may not require a semiconductor for proper operation. The mechanical switch may in particular be adapted to switch an electric power of at least 50 Watts. Mechanical switches are typically widely available, robust and inexpensive. The first switch may for example be used to limit a forward movement of the plunger. Therefore the first motor may be stopped when the plunger has reached the forward position. The forward position is preferably a predetermined absolute position in the device. For example the forward position may be located adjacent a mechanical end position of the plunger in which further advancement is inhibited. Therefore overload of the motor may be prevented that may otherwise occur due to powering the motor against the blocked plunger in its mechanical end position. Further the backward position may be a predetermined absolute position in the device. Thus also the backward movement of the plunger may be limited to avoid damage to the device.

In another embodiment the backward position is a predetermined relative position from a variable starting position from which the plunger is retracted. This preferably provides for a relative retraction stroke of the plunger over a predetermined distance, rather than a stroke to a predetermined absolute position in the device. If the device is used to dispense the material components the plunger may be moved toward the forward position. Thus the less material remains in the containers of the device the closer is the plunger typically positioned toward the forward position. The relative retraction stroke may allow the plunger to be refracted only over a relatively short distance rather than to an eventually far remote absolute position. Thus at the next use of the device to dispense material the plunger needs to be moved only over a relatively short distance until further material can be dispensed. Therefore time may be saved for repositioning the plunger particularly when the device is intermittently used. Further the material component(s) that is/are pressurized for dispensation thereby may be released to prevent afterflow of the material(s).

In one embodiment the first and second mechanical switches preferably are Normal Closed Contact (NCC) switches. Therefore the first and second switches may be open when activated, and may be closed when inactivated or released. The first and second switches may for example reset automatically to the inactivated state. The first and second switches may be activated at certain positions of the plunger. In particular the first switch may be activated when the plunger is positioned at about the forward position, but may otherwise be inactivated. Further the second switch may be activated when the plunger is positioned at about the backward position, but may be otherwise inactivated. In this way a relatively robust and inexpensive control of the device may be provided.

In another embodiment the device further has at least one piston. The piston and the plunger are preferably movable relative to one another between a first positional limit and a second positional limit. The piston and the plunger are preferably movable along an axis that is generally parallel to or congruent with an axis on which the plunger can be advanced or retracted. This embodiment may allow for a relative retraction stroke of the plunger. For example the piston and the plunger may initially be positioned at the first positional limit relative to one another. When the device is used for dispensing material the plunger and the piston may move together until the piston reaches the material. A further movement of the plunger then preferably causes the piston to move relative to the plunger because the piston may be impeded in further movement by the material. Thus the piston may move relative to the plunger from the first positional limit toward the second positional limit. At the second positional limit further relative movement between the piston and the plunger is preferably inhibited so that further advancing the plunger also advances the piston, causing the material to be extruded. The device may be adapted such that at about the second positional limit the second switch is triggered to close. For example the second switch may be an NOC switch which is activated at about the second positional limit, but inactivated offset about the second positional limit. Because the first electric circuit may be selected for dispensing the material the setting of second switch (being part of the second electric circuit) has preferably no effect as long as the device is used to dispense further material. However as soon as the second electric circuit is selected, for example because a user operates the selector switch accordingly, the second switch enables the retraction of the plunger because it is preferably closed in this position. However the retraction of the plunger may cause the piston and the plunger to move away from one another, for example due to spring load between the piston and the plunger. Thus as the piston and the plunger are positioned further toward the first positional limit the second switch may open and cause the retraction to stop.

The device may further have two pistons which cooperate with the plunger as described although the invention may be implemented likewise with one piston of the embodiment above. For example the device may have one piston which is movable relative to the plunger between the first and second positional limits, and a further piston which is fixed at the plunger. The movable piston may at the first positional limit protrude over the fixed piston, and may be co-aligned with the fixed piston at the second positional limit. Therefore substantial simultaneous extrusion of the individual components may be achieved.

In one embodiment the device further has a second motor for driving a mixer for mixing the dental material. The second motor and the first motor are preferably in parallel connection in the first circuit. Further the second motor may be short cut in the second circuit. Therefore the mixer may be driven during forward advancement of the plunger to dispense material, but may be stopped when the plunger is retracted. Therefore unnecessary mixing of material in the mixer may be avoided while the plunger is retracted, which may cause altering or premature hardening of the material in the mixer.

In another embodiment the device comprises a third switch in parallel connection to the second switch. Therefore the third switch may be used to bridge or short cut the second switch. This may be useful particularly in embodiments in which the relative retraction stroke is implemented. For example the second switch causing the retraction stroke to stop eventually remote from a backward position may be bridged to further or entirely retract the piston toward the back end position. This may allow for moving the plunger away from the containers, for example to enable the containers to be exchanged.

In still another embodiment the device comprises a fourth switch in serial connection to the third switch, and with the series of the third and fourth switch being in parallel connection to the second switch. The fourth switch may for example be used as an end switch at the backward position of the plunger. This embodiment may particularly used in combination with embodiment having the third switch for bridging the second switch because the fourth switch preferably stops the retraction stroke adjacent backward position of the plunger even though a user uses the third switch for retracting the plunger. Thus damage due to driving the plunger against its backward position may be avoided.

In one embodiment the device comprises a first power supply. The first power supply may be an interface to an external power supply, for example. Further the power supply may comprise a transformer which is adapted to transform external power to a desired internal power of the device. The internal power preferably is adapted for directly powering the first motor and/or the second motor. A further suitable power supply may have at least one battery (for example a rechargeable battery). The first and/or the second motor(s) may be direct current (DC) motor(s). Accordingly the first power supply may provide a direct current power suitable to drive the first and/or the second motor(s). Preferably the first switch and/or the second switch are used to switch the power provided by the first power supply, meaning that the first and/or second switches are preferably arranged in the load circuit of the first motor and/or the second motor. Further preferably the first and/or second switch(es) operate without additional power, for example do not require any control power, like a transistor or the like would require. Therefore the first power supply may be relatively simple and inexpensive. The skilled person will recognize that multiple types of motors and corresponding appropriate power supplies may be used in a similar manner.

In another embodiment the first electric circuit provides a first polarity of the first power supply relative to the first motor, and the second electric circuit provides a reversed second polarity of the first power supply relative to the first motor. Therefore the first and second electric circuits preferably provide for powering the motor such that it moves in opposite directions respectively. Accordingly the first and second electric circuits therefore may also provide for driving the plunger opposite directions respectively.

In one embodiment the second electric circuit comprises a second power supply which is disconnected in the first electric circuit. The second power supply may be in serial connection with the first power supply. Thus the voltage in the first electric circuit may be increased relative to the second electric circuit, for example doubled. Thus the first motor may be powered at a higher voltage in the first electric circuit relative to the second electric circuit. Accordingly the first motor may move at a higher speed when powered by the first electric circuit relative to the second electric circuit. Thereby the plunger may be more rapidly retracted than advanced. The plunger may for example be advanced at a speed that is appropriate for dispensing of the material. The retraction of the plunger at a higher speed may for example save time when a container is to be replaced in the device because the plunger is retracted from the container more rapidly.

DETAILED DESCRIPTION OF THE INVENTION

Figure 1:
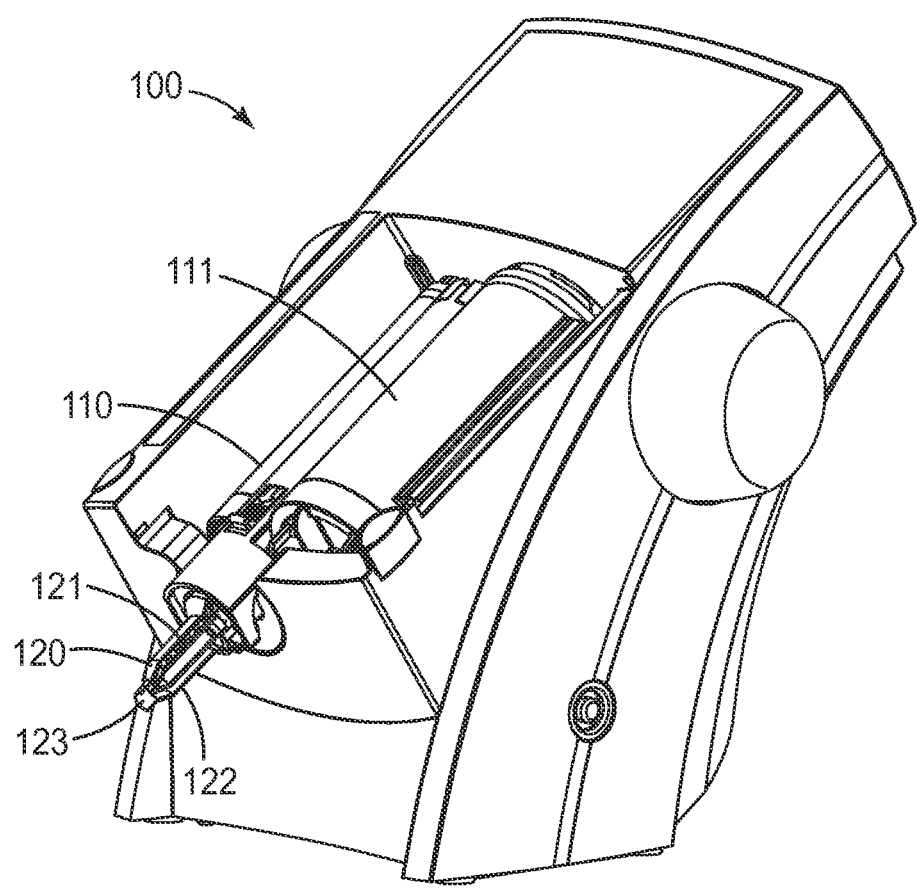
FIG. 1 is a perspective view of a dispensing device for dental materials.

FIG. 1 shows a device 100 for mixing and dispensing dental materials. The device is motorized and therefore allows for automatic dispensation of the materials. A similar device is available under the designation 3M™ ESPE™ Pentamix™ from 3M ESPE AG, Germany. The device 100 holds two components of a dental material in containers 110, 111. A mixer 120 for mixing the two components is attached to the device 100. The mixer 120 has a mixing chamber formed between a rotatable mixing rotor 121 and a mixer housing 122. The mixer is connected with the containers 110, 111 such that the individual components can flow into the mixing chamber. The mixture can exit through an outlet 123 of the mixer 120. The device 100 is adapted to drive the mixing rotor 121 so as to mix the components in the mixing chamber. The device 100 implements a continuous dynamic mixing process in which components can be continuously supplied into the mixing chamber and in which the mixture from the components can be dispensed continuously from the mixer. Thus the device allows preparation for variable amounts of dental materials without the need of pre-determining amounts of initial components of the mixture. The components can be advanced toward the mixer 120 by a plunger (not shown) of the device 100. Both the mixer and the plunger can be driven by a motor, or individual motors, in the device 100. The device therefore further has a power supply for powering the motor or motors. Possible power supplies of the device may for example include an electric battery, an electric transformer, or an electric interface to an outside power supply.

The device shown may be used to mix and dispense a hardenable dental impression material, for example. The mixed material may be used to fill a dental tray which is then placed into a patient's mouth to take a dental impression. The mixer is attached replaceably to the device 100. Therefore when the mixed material hardens and thus blocks the mixer the used mixer may be replaced by an unused mixer for the next use of the device.

Figure 2:
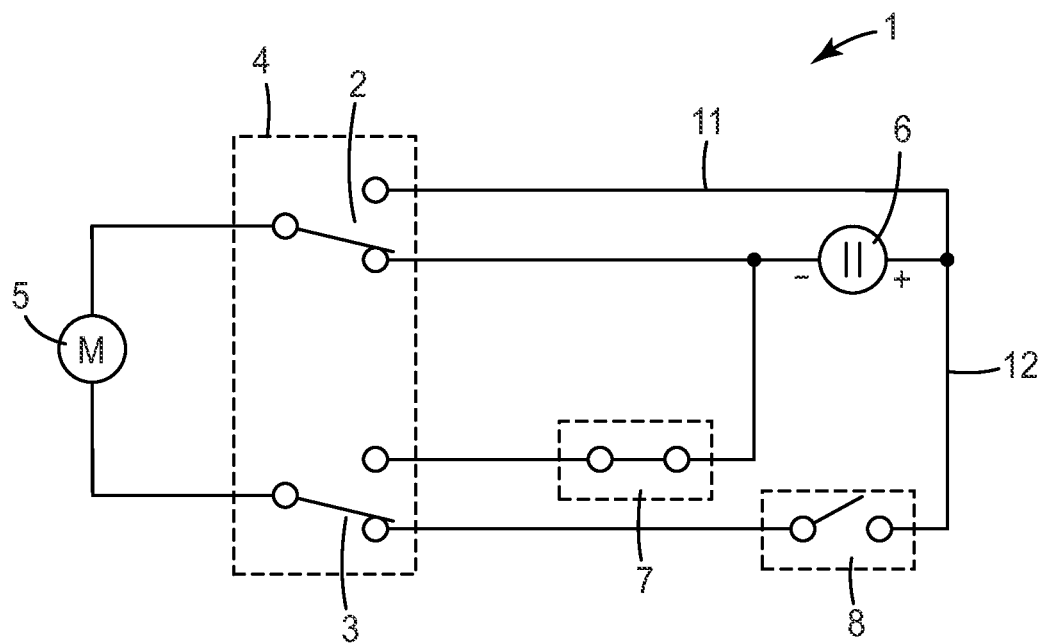
FIG. 2 is a circuit diagram of a control circuitry for controlling a dispensing device for dental materials according to an embodiment of the invention.

FIG. 2 is a circuit diagram of a control circuitry 1 for controlling a dispensing device according to the invention. The control circuitry 1 comprises a first motor 5 and a power supply 6 for powering the first motor 5. The first motor 5 may for example be used to drive a plunger of the device. The control circuitry 1 further comprises switches for powering the first motor in different modes or for switching the first motor off. This is explained in more detail in the following.

The control circuitry 1 comprises a first dual pole (DP) switch 2 and a second dual pole (DP) switch 3 which preferably together form a dual pole double throe (DPDT) switch 4, also referred to as "selector switch" herein. The first and second DP switches 2, 3 are arranged in the control circuitry 1 to alternately power the first motor 5 at opposing polarities by the power supply 6. Thus the first motor may move in opposite directions, for example to advance the components of the dental material or to retract from the components of the dental material. The DPDT switch preferably is adapted to jointly switch the first and second DP switches when the DPDT switch is operated. The skilled person will recognize that jointly switching the first and second DP switches may include simultaneous or sequential switching of both switches, but with the DPDT switch being operated only once. A sequential switching may for example provide for an electric circuit being opened before another circuit is closed, and thereby may prevent a short circuit during switching.

The control circuitry 1 in the configuration shown has a first electric circuit 11 and a second electric circuit 12 which can be alternately selected by operation of the first and second DP switches 2, 3. In particular the first and second DP switches 2, 3 are arranged in the control circuitry 1 to alternately close a connection in one of the first and second electric circuits 11, 12 and thereby to open a connection in the respective other electric circuit 11 or 12. The electric circuit in which the first and/or second DP switches 2, 3 open a connection therefore is interrupted, and thus is disabled from powering the first motor 5. Further the power supply 6 and the first motor 5 are arranged relative to each other at reversed polarities in the first and second electric circuits 11, 12. Therefore the first motor 5 preferably moves in opposite directions when powered by the first and the second electric circuits 11, 12 respectively. Accordingly the control circuitry 1 may provide for driving the plunger of the device in opposite directions for advancing the dental material or retracting from the dental material depending on the setting of the selector switch.

The control circuitry 1 further comprises a first switch 7, and a second switch 8. In particular the first switch 7 is arranged in the first electric circuit 11. The first switch 7 thus allows for closing or opening of the first electric circuit 11 when the first electric circuit 11 is selected via first and second DP switches 2, 3. The second switch 8 is arranged in the second electric circuit 12, and allows for closing or opening of the second electric circuit 12 when the second electric circuit 12 is selected via first and second DP switches 2, 3. In the example shown in FIG. 2 the second electric circuit 12 is selected, and as a result the first electric circuit 11 is interrupted. Further the second switch 8 is open so that also the second electric circuit 12 is interrupted. Consequently the first motor 5 is not powered in the situation shown in the FIG. 2.

Figure 3:
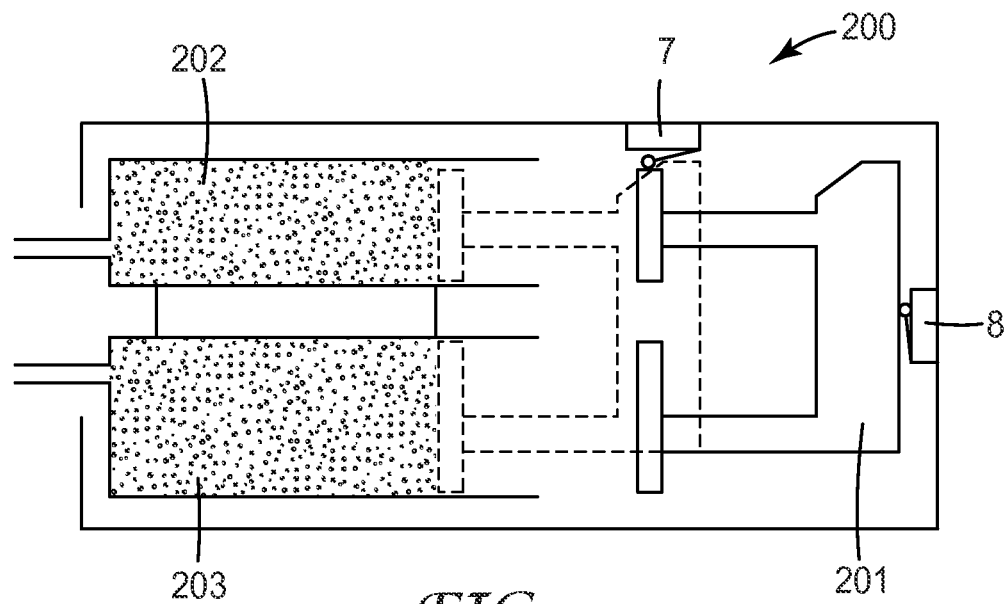
FIG. 3 is a schematic view of a dispensing device for dental materials according to an embodiment of the invention.

FIG. 3 illustrates an exemplary arrangement of the first and second switches 7, 8 in a device 200 for dispensing a dental material. The device 200 has a plunger 201 which is adapted to move into containers 202, 203 for advancing components in the containers 202, 203 toward a mixer (not shown). In the situation shown the plunger 201 is refracted from the components and positioned at a backward position of the plunger. The backward position in the example corresponds to a rear end position of the plunger in the device. In the backward position of the plunger the second switch 8 is activated. In the example the second switch 8 is a normally closed contact (NCC) switch which is closed in an inactivated stage, but is open in an activated stage. The skilled person will know that the illustrated principle may be implemented in many different ways, for example by use of a normally open contact (NOC) switch which is arranged in the device such that it is inactivated (switch open) in the end position of the plunger, but activated (switch closed) otherwise.

The first switch 7 preferably is also a NCC switch. However the skilled person will be able to also replace the first switch by a NOC switch by adopting the device appropriately to achieve the same function. The first switch 7 in the example is inactivated in the backward position of the plunger (switch closed), and further is preferably activated (switch open) in a forward position of the plunger, indicated by the dashed lines. The forward position in the example corresponds to a front end position of the plunger in the device. Preferably the first switch 7 is further inactivated between the rear and the forward position of the plunger. FIG. 3 may therefore show a situation which corresponds to the situation illustrated in FIG. 2 in which the first switch 7 is closed, the second switch 8 is open, and the selector switch 4 selects the second electric circuit. Thus the device 200 in FIG. 3 may be switched off and in an initial position.

FIGS. 4a-9a illustrate different modes of operation of the control circuitry 1 and FIGS. 4b-9b illustrate corresponding operational stages of the dispensing device 200.

Figure 4A:
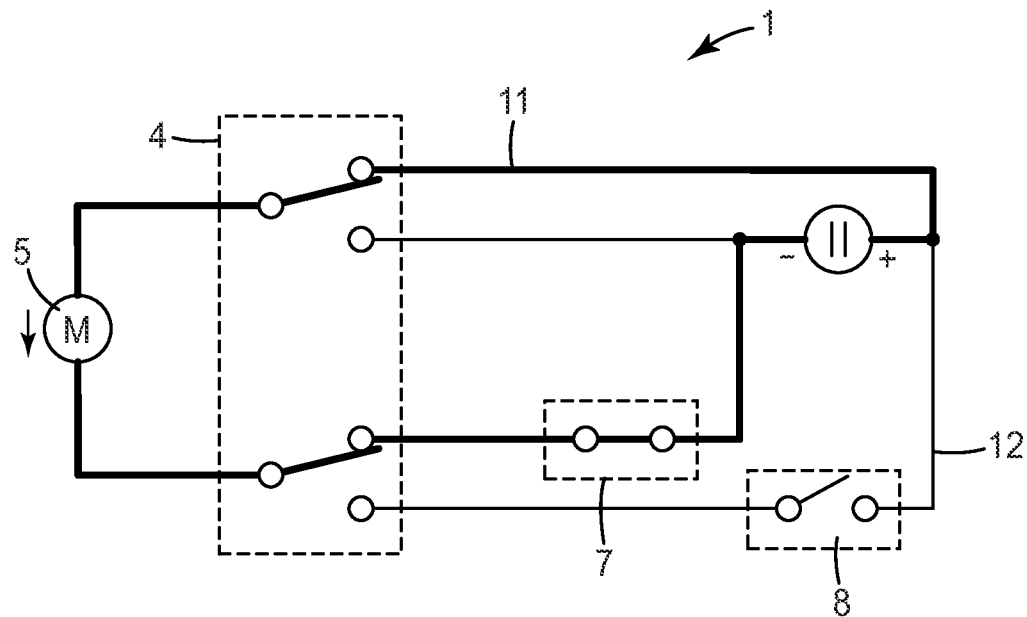
FIG. 4a is a circuit diagram of the control circuitry shown in FIG. 2 at another stage of operation according to an embodiment of the invention.
Figure 4B:
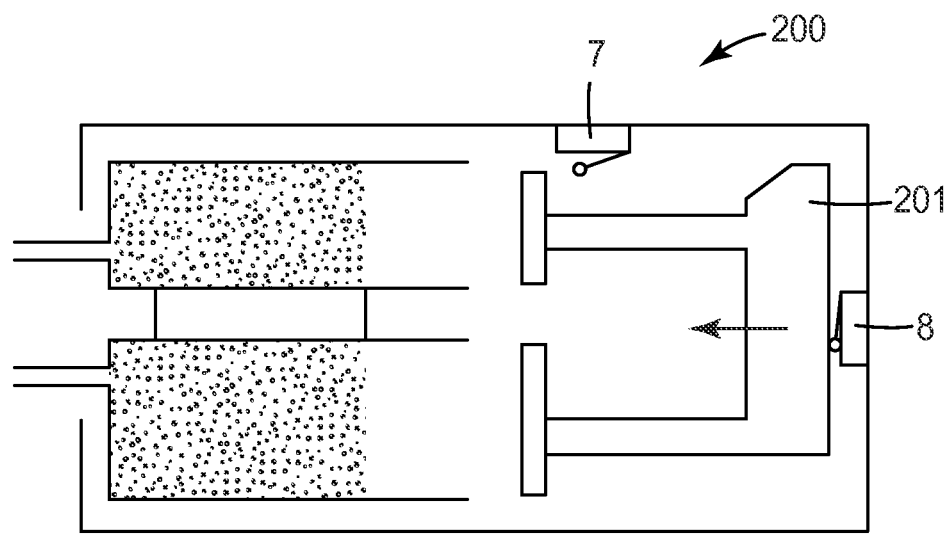
FIG. 4b illustrates the stage of operation of the device shown in FIG. 3 which relates to the stage of operation of the control circuitry shown in FIG. 4a according to an embodiment of the invention.

In FIG. 4a the selector switch 4 selects the first electric circuit 11, and the first switch 7 is closed. Therefore the first motor 5 is powered by the first electric circuit 11. As indicated in FIG. 4b (see arrow) the first motor 5 in the power mode provided by the electric circuit 11 causes the plunger 201 to move forward in a direction toward the material components which corresponds to a direction toward the forward position of the plunger 201. In the situation shown the plunger 201 is still in about the backward position so that the second switch 8 in the second electric circuit 12 is still open.

Figure 5A:
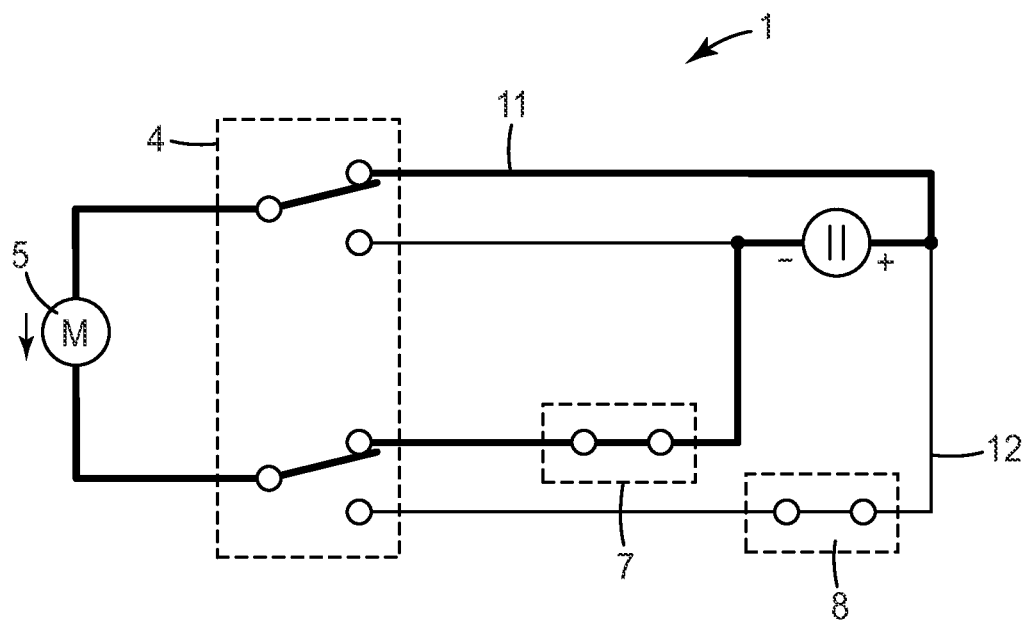
FIG. 5a is a circuit diagram of the control circuitry shown in FIG. 4a at a further stage of operation according to an embodiment of the invention.
Figure 5B:
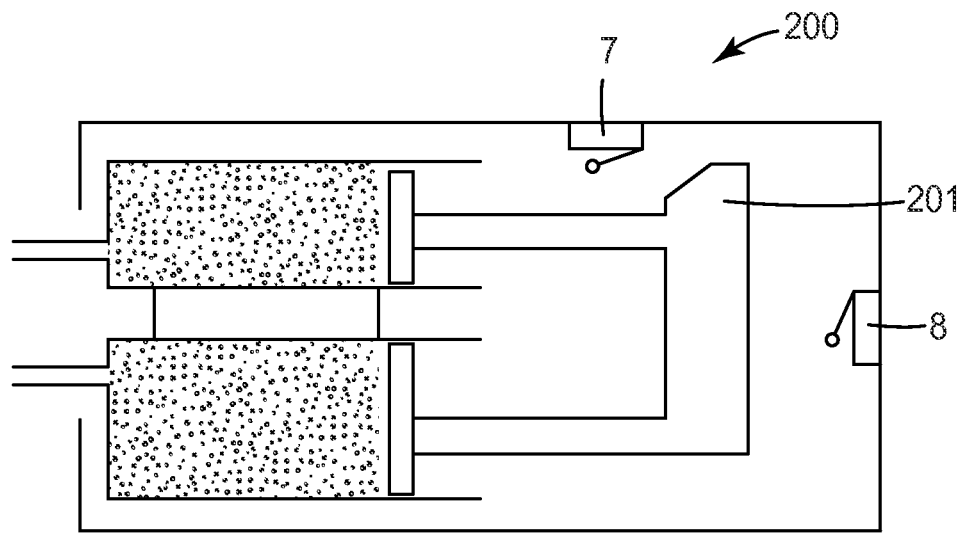
FIG. 5b illustrates the stage of operation of the device shown in FIG. 4b which relates to the stage of operation of the control circuitry shown in FIG. 5a according to an embodiment of the invention.

However in FIG. 5a the second switch 8 is closed because the plunger 201 is positioned further to the forward position as illustrated in FIG. 5b. The selector switch 4 in FIG. 5a still selects the first electric circuit 11 so that the second electric circuit 12 is interrupted. Therefore the second electric circuit 12 is inactive although the second switch 8 is closed. Because the plunger 201 (FIG. 5b) has not reached the forward position the first switch 7 is not activated and thus is closed. Accordingly the first electric circuit 11 powers the first motor 5, thus causing the plunger 201 to move further forward. However in case the selector switch 4 would be operated to select the second electric circuit 12, the first motor 5 would be powered at reverse polarity such that the plunger 201 would be retracted.

Figure 6A:
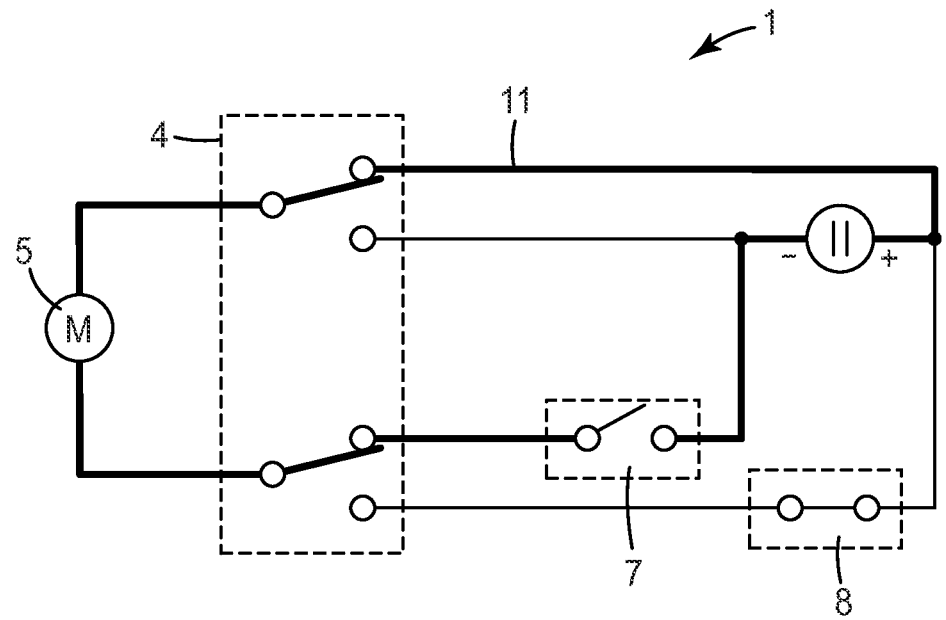
FIG. 6a is a circuit diagram of the control circuitry shown in FIG. 5a at a further stage of operation according to an embodiment of the invention.
Figure 6B:
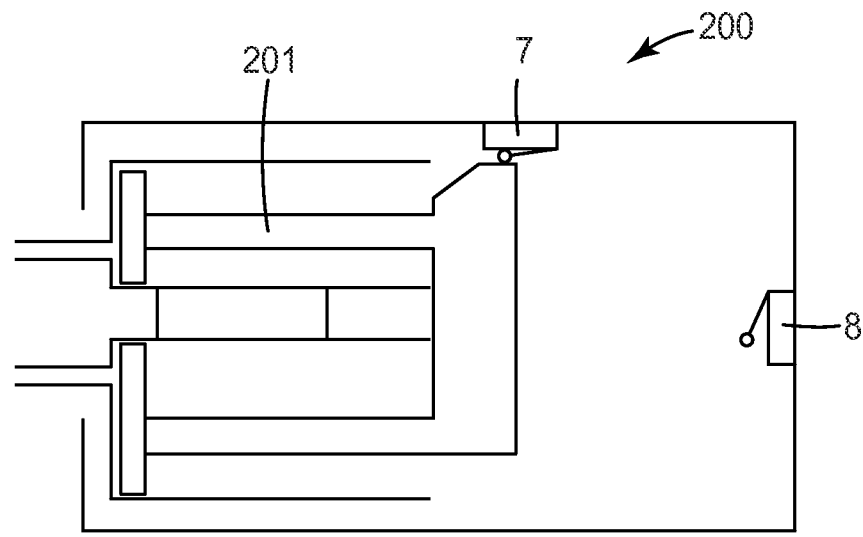
FIG. 6b illustrates the stage of operation of the device shown in FIG. 5b which relates to the stage of operation of the control circuitry shown in FIG. 6a according to an embodiment of the invention.

In FIG. 6b the plunger 201 of the device 200 is positioned at the forward position and therefore the first switch 7 is activated and thus is open. As illustrated in FIG. 6a therefore the first electric circuit 11 of the electric circuitry 1 is open and consequently the first motor 5 is off.

The first switch 7 may be an end switch which prevents further movement of the plunger 201, for example when a user continues operating the selector switch 4 for dispensing further material although the plunger 201 has reached the front end position. Thus damage to the device and/or the first motor 5, for example due to overload, maybe prevented.

Figure 7A:
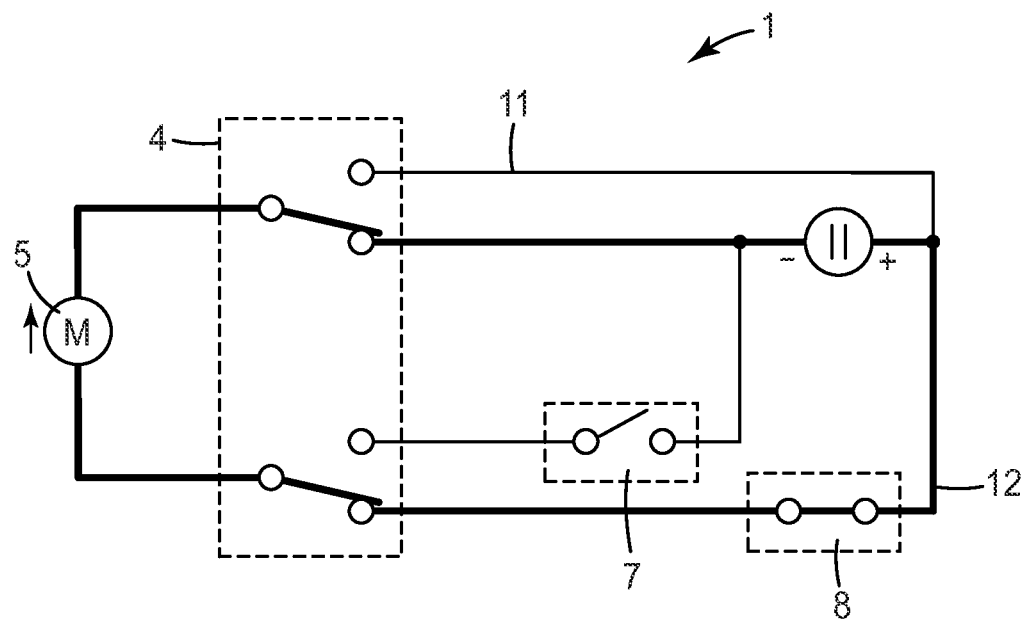
FIG. 7a is a circuit diagram of the control circuitry shown in FIG. 6a at a further stage of operation according to an embodiment of the invention.

FIG. 7a shows a situation in which the selector switch 4 selects the second electric circuit 12. With the second switch 8 being closed the second electric circuit 12 is closed and therefore powers the first motor 5. The first motor 5 when powered by the second electric circuit 12 moves in an opposite direction of the direction the first motor moves when powered by the first electric circuit 11. Therefore as indicated in FIG. 7b (see arrow) the plunger 201 is retracted from the material components, meaning the plunger 201 moves in a direction toward the backward position of the plunger.

Figure 7B:
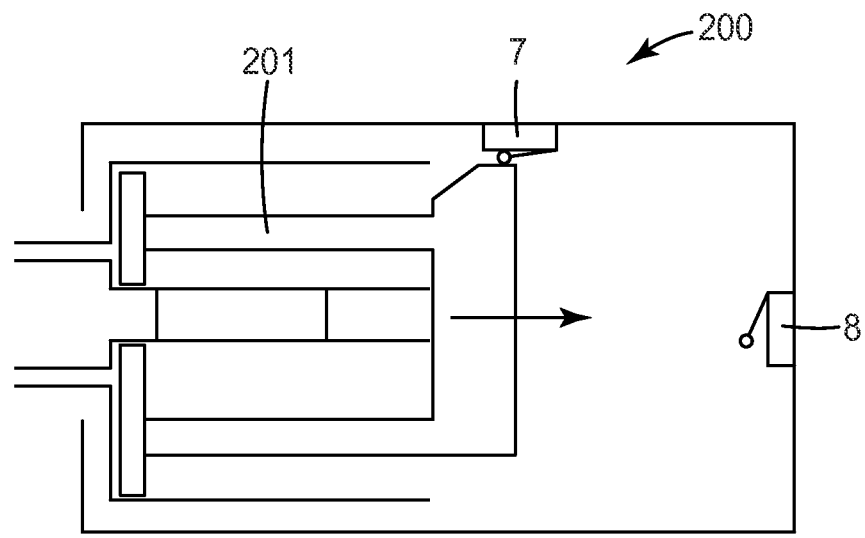
FIG. 7b illustrates the stage of operation of the device shown in FIG. 6b which relates to the stage of operation of the control circuitry shown in FIG. 7a according to an embodiment of the invention.
Figure 8A:
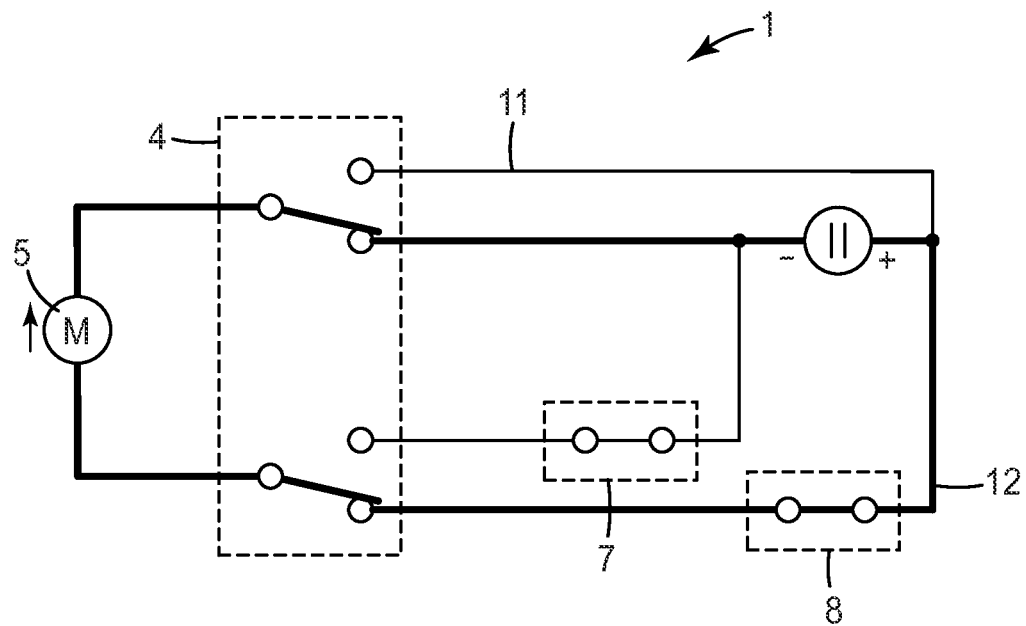
FIG. 8a is a circuit diagram of the control circuitry shown in FIG. 7a at a further stage of operation according to an embodiment of the invention.
Figure 8B:
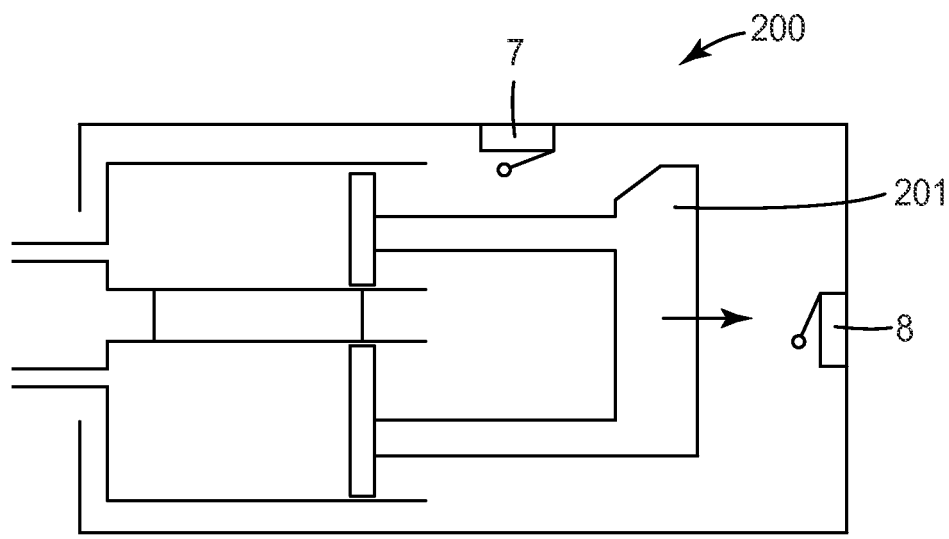
FIG. 8b illustrates the stage of operation of the device shown in FIG. 7b which relates to the stage of operation of the control circuitry shown in FIG. 8a according to an embodiment of the invention.

FIG. 8b shows the device 200 with the plunger 201 positioned further toward the backward position relative to the situation illustrated in FIG. 7b. At the position of the plunger shown the plunger has moved away from the first switch 7 such that the first switch 7 is closed. This has however no impact on the operation mode of the first motor 5 in the situation shown because the first switch 7 is part of the first electric circuit 11 which is inactive.

Figure 9A:
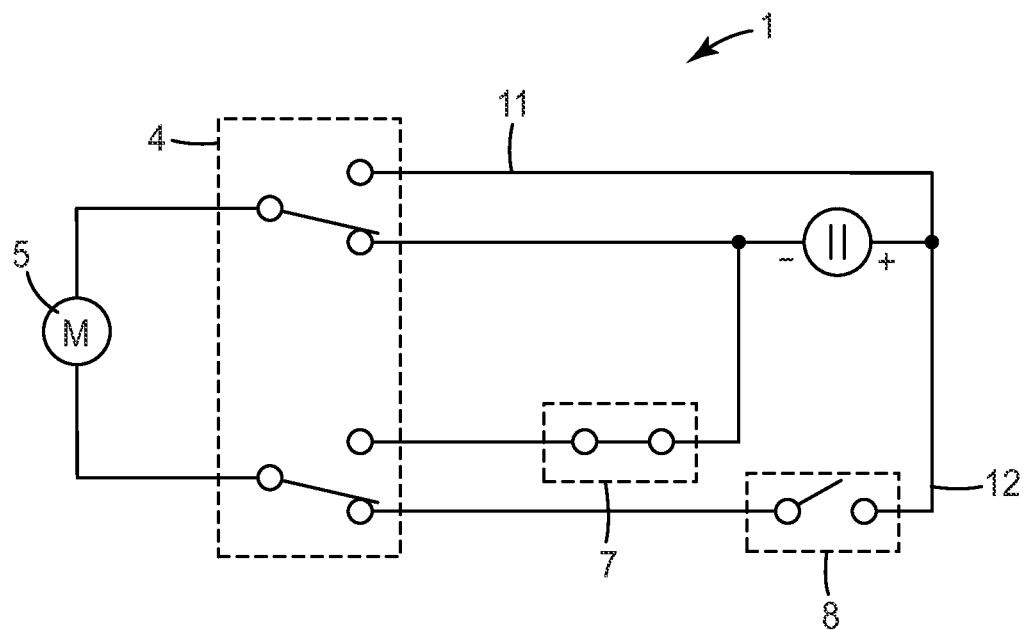
FIG. 9a is a circuit diagram of the control circuitry shown in FIG. 8a at a further stage of operation according to an embodiment of the invention.
Figure 9B:
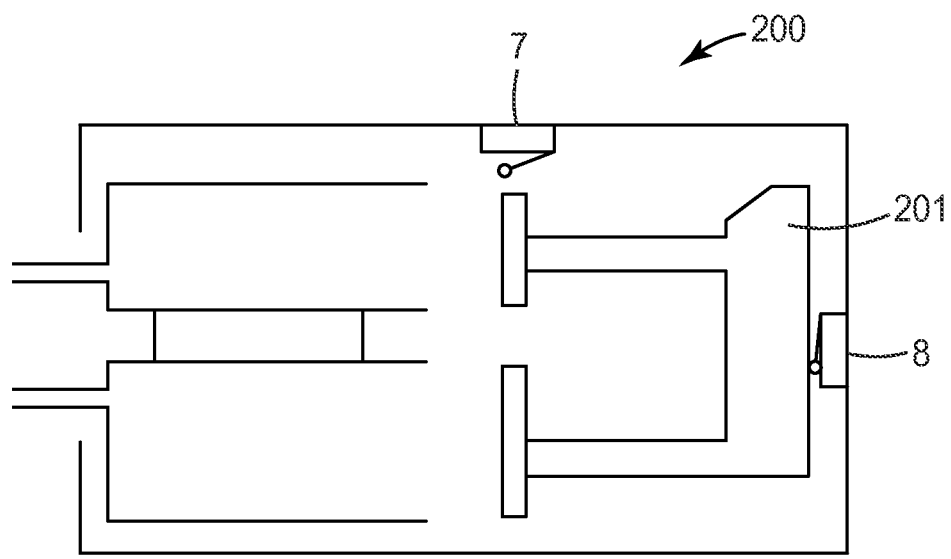
FIG. 9b illustrates the stage of operation of the device shown in FIG. 8b which relates to the stage of operation of the control circuitry shown in FIG. 9a according to an embodiment of the invention.

FIGS. 9a and 9b corresponds to the situation shown in FIGS. 4a and 4b, but with the selector switch 4 selecting the second electric circuit 12, for example due to the selector switch 4 being released.

The selector switch 4 may further provide for interrupting both the first and the second electric circuits 11, 12 at the same time and therefore may have three different settings. Further the setting which interrupts the first and the second electric circuits at the same time may be the normal setting of the selector switch to which the switch automatically resets when not operated. This may allow for an automatic stop of the device at any position of the plunger during dispensing material or during retracting the plunger as the selector switch is released.

The selector switch 4 preferably automatically resets to normally select the second electric circuit when not operated, and preferably must be operated to select the first electric circuit. Therefore preferably the device is adapted such that the plunger automatically returns toward the backward position when the selector switch is released.

Figure 10:
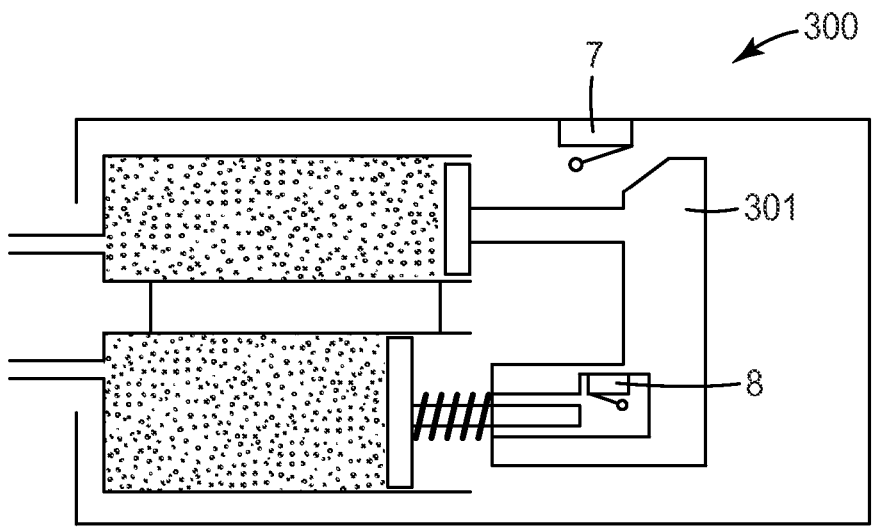
FIG. 10 is a schematic view of the dispensing device shown in FIG. 3 at another stage of operation.

In an embodiment shown in FIG. 10 the second switch 8 is arranged in a device 300 so that the backward position of the plunger is dragged in a predetermined distance behind the forward movement of the plunger. Therefore when a forward movement of the plunger is stopped the plunger may from its current position automatically retract over a predetermined relative distance rather than to an absolute position. In other words the plunger does not always automatically return to the back end position, but may retract only over a predetermined distance relative to a starting position from which the plunger is retracted. Thereby the components of the dental material may be dispensed, and as the dispensation is stopped the plungers may retract a little to release the components from pressure exerted for dispensing. Thus afterflow of the components upon stopping dispensation of material may be prevented. The device 300 further comprises the first switch 7 which is activated when the plunger reaches the front end position.

Figure 11A:
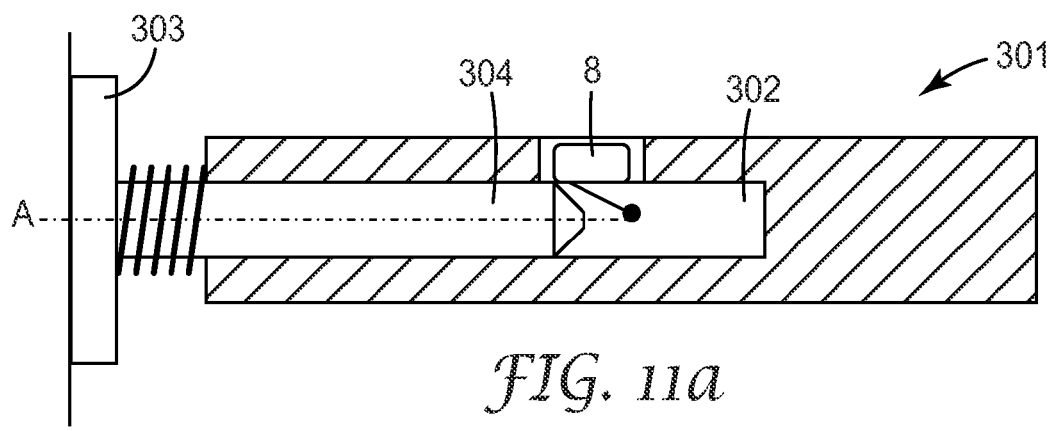
FIGS. 11a, 11b are detail views of a plunger at different operational stages of a dispensing device according to an embodiment of the invention.
Figure 11B:
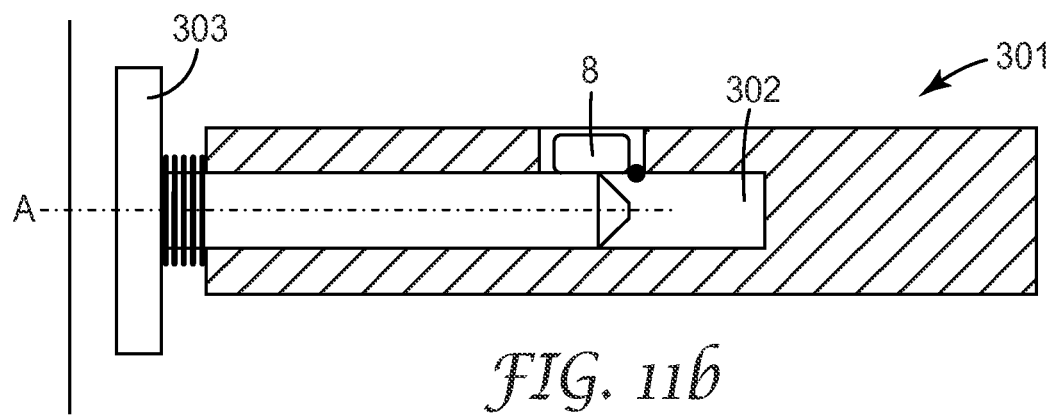

The plunger 301 of FIG. 10 is shown in greater detail in FIGS. 11a and 11b. The plunger 301 has a receptacle 302 in which a piston 303 is received. The piston 303 and the plunger 301 are movable relative to one another along a longitudinal axis A. The longitudinal axis A preferably substantially corresponds to the direction in which the plunger can be advanced or refracted in the device 300. In the example the piston 303 is telescopically guided in the receptacle 302 of the plunger 301. Near a back end 304 of the piston 303 the second switch 8 is arranged such that the piston 303 can activate the second switch 8 depending on the longitudinal position of the piston relative to the plunger. The piston and the plunger are preferably urged toward an initial position relative to each other by spring load. In the initial position of the piston 303 relative to the plunger 301 the second switch 8 is released. The second switch 8 of this example is a NOC switch which in the released setting is open. The initial position of the piston and the plunger relative to one another may for example correspond to a position in which the plunger and the piston are retracted from the material components. FIG. 11b illustrates the position of the piston and the plunger relative to one another, when the plunger forces the piston forward to advance a material component. At this stage the piston may be positioned closer toward the plunger so that the second switch 8 is activated and thus closed. The second switch 8 when closed enables the first motor to be powered to retract the plunger. As the plunger is retracted from the position shown in FIG. 11b the piston is moved away from the plunger by spring load, and further the piston releases the second switch 8 (see FIG. 11a), thus causing the second switch 8 to open and stopping further movement of the plunger.

Figure 12:
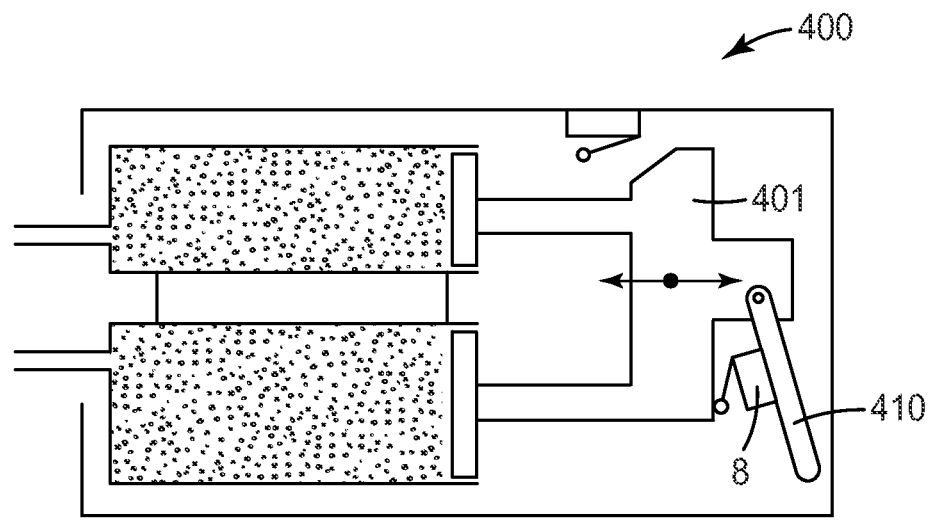
FIG. 12 is a schematic view of another embodiment of a dispensing device for dental materials according to the invention.

FIG. 12 shows a device 400 implementing an alternative embodiment for a relative retraction stroke based on a variable starting position. The device has a lever 410 which is pivotally attached at a first end to the plunger 401. The lever 410 has a free second end which may for example abut at a linear guide in the device. The lever 410 is preferably arranged in the device such that it can be dragged behind the plunger with the free end sliding along the guide when moved forward with the plunger, but when pushed backward blocks or clamps with the guide. Therefore when the plunger is retracted or moved backwards the lever may move towards the plunger. The second switch 8 may for example be arranged between the plunger 401 and the lever 410 as shown. Thereby the switch 8 may be activated during retraction of the plunger, but released during forward movement of the plunger. Thus the device 400 may allow the plunger 401 to be advanced to a desired position, but may be adapted to stop the plunger 401 relatively shortly after initiating retraction.

Figure 13:
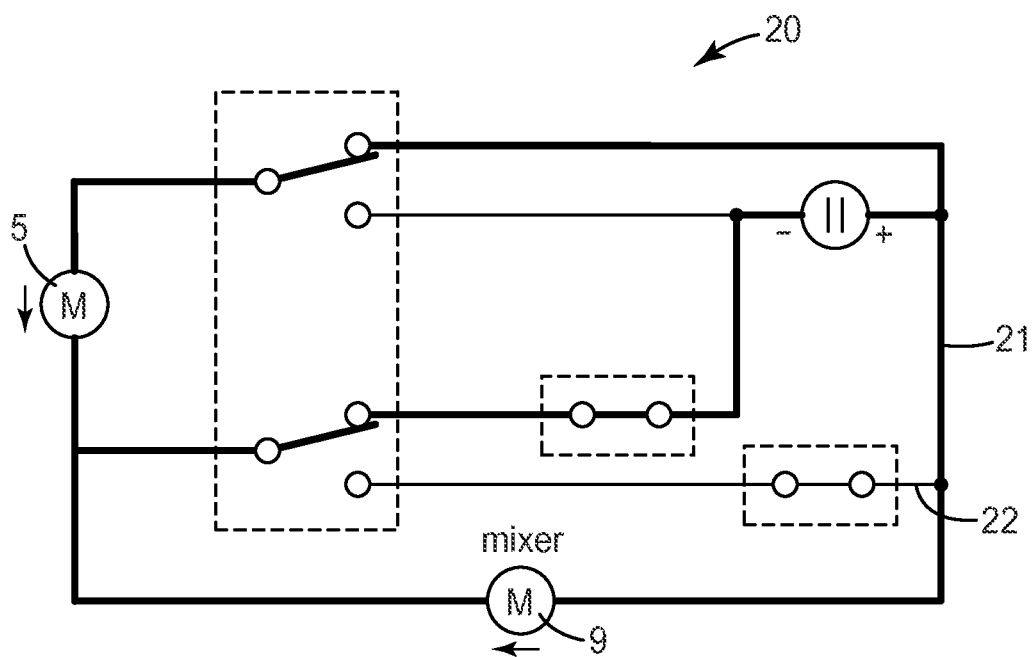
FIG. 13 is a circuit diagram of a control circuitry for controlling a dispensing device for dental materials according to another embodiment of the invention.

FIG. 13 shows a control circuitry 20 which comprises the features of the control circuitry 1 shown in FIG. 2 but additionally comprises a second motor 9. The second motor 9 is in parallel connection to the first motor in a first electric circuit 21, but is shorted in the second electric circuit 22. The second motor 9 preferably is used to drive a mixer for mixing material components. Thus the mixer is driven together with moving the piston to advance material components toward the mixer, but is not driven when the plunger is retracted. Therefore the remaining material components in the mixer may not be agitated during retraction of the plunger when material supply in the mixer discontinued. This may prevent the remaining material from undue intense mixing and thus from premature hardening and blocking the mixer.

Figure 14:
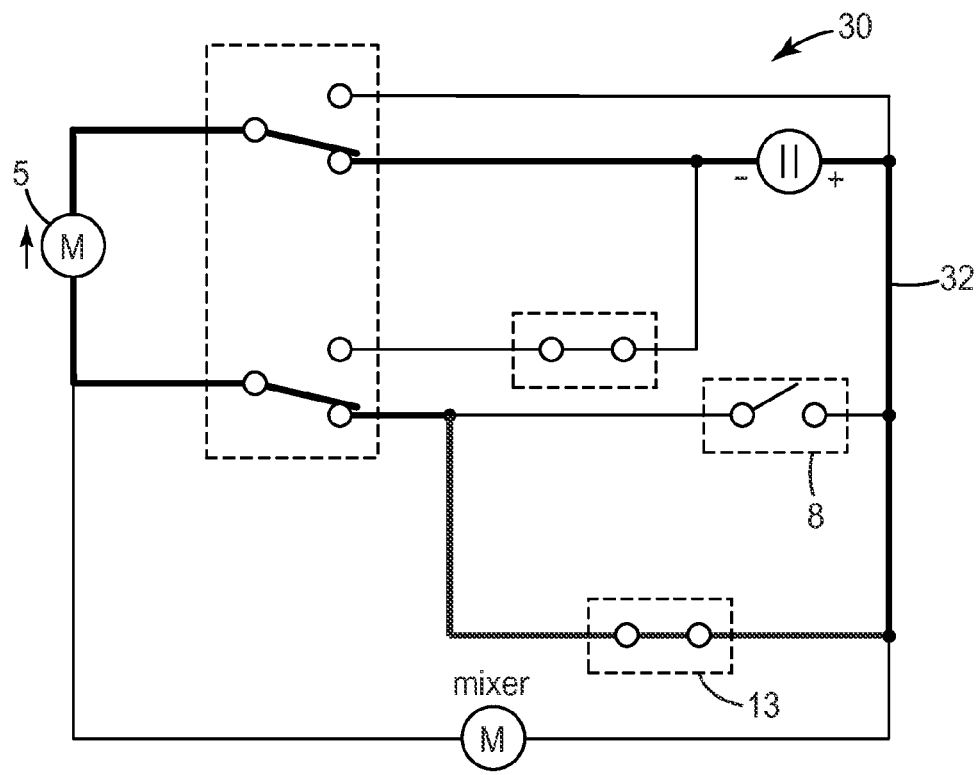
FIG. 14 is a circuit diagram of a control circuitry for controlling a dispensing device for dental materials according to a further embodiment of the invention.

FIG. 14 shows a further control circuitry 30 which comprises the features of the control circuitry 20 shown in FIG. 13 but additionally comprises a third switch 13. The third switch 13 is parallel connected to the second switch 8. Therefore when the second switch 8 is open and the second electric circuit 32 is selected as shown, the third switch may be used to bridge the second switch and thus close second electric circuit 32. In this way the first motor 5 can be powered to retract the plunger although the second switch 8 is open. This may allow for retracting the plunger toward the backward position in embodiments which implement the relative retraction stroke. This may for example facilitate exchanging containers in the device, because the control circuitry 30 may allow for motorized retraction of the plungers which otherwise may have to be performed manually.

Figure 15:
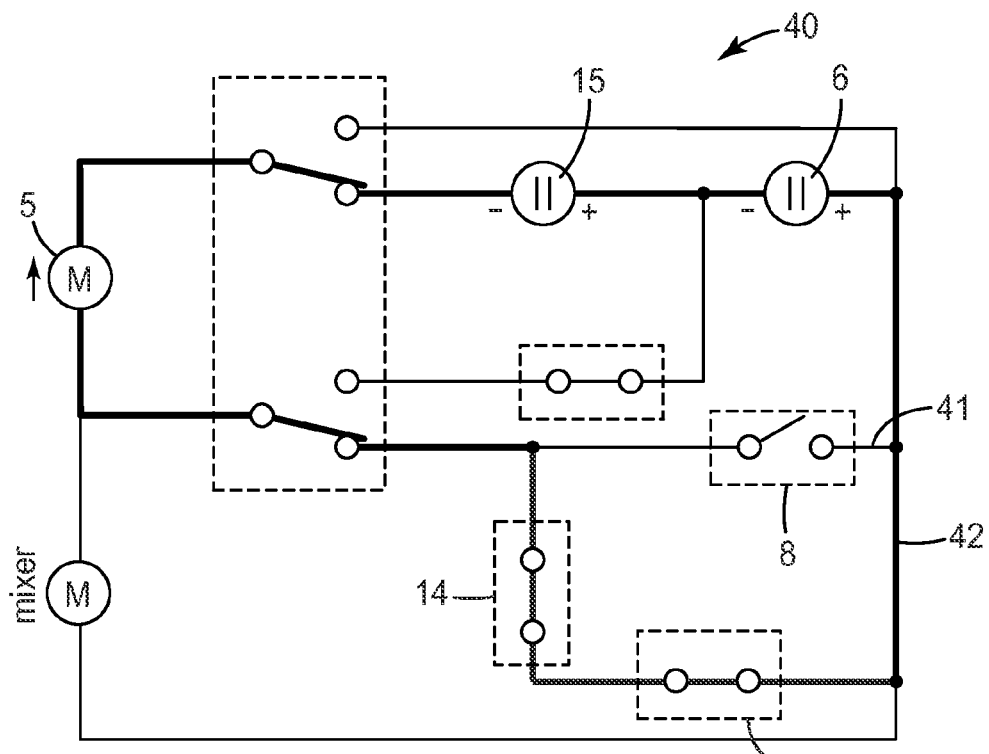
FIG. 15 is a circuit diagram of a control circuitry for controlling a dispensing device for dental materials according to still another embodiment of the invention.

FIG. 15 shows a further control circuitry 40 which comprises the features of the control circuitry 30 shown in FIG. 14 but in addition to the first power supply 6 comprises a second power supply 15 as well as optionally a fourth switch 14. The fourth switch 14 is serially connected to the third switch 13. Therefore if the third switch 13 is used to retract the plunger the fourth switch 14 may interrupt the second electric circuit 42 as the plunger reaches the back end position. Therefore damages at the device may be prevented as a user continues using the third switch 13 to retract the plunger although the plunger has reached its back end position. The second power supply 15 is arranged in the second electric circuit 42, and serially connected to the first power supply 6. Therefore the voltage within the second electric circuit 42 is increased, for example doubled, so that the motor 5, powered by the second electric circuit 42, preferably moves at a higher speed.

The second power supply is not connected in the first electric circuit 41 so that the motor preferably runs at different speeds in the first and the second electric circuits 41, 42. Thus the device may be adapted to advance the plunger at a first speed and retract the plunger at a second speed. The second speed may be greater than the first speed so that material can be appropriately dispensed and mixed, but the plunger can be rapidly retracted, for example for exchanging the containers in the device.

We claim:

1. A device for dispensing a dental material, comprising:
    a plunger for extruding at least a component of the dental material from a container;
    a first motor cooperating with the plunger;
    a first electric circuit which is adapted for powering the first motor to advance the plunger forward for extruding the material component;
    a second electric circuit which is adapted for powering the first motor to retract the plunger backward from the material;
    a selector switch which is adapted to alternately select the first electric circuit or the second electric circuit for powering the motor;
    a first switch which is arranged within the first electric circuit and being adapted to interrupt the first electric circuit when the plunger is positioned at a forward position;
    a second switch which is arranged within the second electric circuit and being adapted to interrupt the second electric circuit when the plunger is positioned at a backward position, wherein the backward position is a predetermined relative position from a variable starting position from which the plunger is retracted; and
    a piston, the piston and the plunger being movable relative to one another between a first positional limit and a second positional limit along an axis on which the plunger is advanced or retracted, wherein the device is further adapted such that in the second positional limit the second switch is triggered to close.

2. The device of claim 1, being adapted such that the selector switch automatically resets to select the second electric circuit.

3. The device of claim 1, wherein the selector switch is adapted to interrupt the second electric circuit along with closing an interruption in the first electric circuit and thereby to select the first electric circuit, and wherein the selector switch is adapted to interrupt the first electric circuit along with closing an interruption in the second electric circuit and thereby to select the second electric circuit.

4. The device of claim 1, wherein the selector switch comprises a double pole double throw (DPDT) switch, which has at least two double pole (DP) switches.

5. The device of claim 1, wherein the first or second switch comprises a mechanical switch.

6. The device of claim 1, wherein the forward position is a predetermined absolute position in the device.

7. The device of claim 1, further having a second motor for driving a mixer for mixing the dental material, wherein the second motor and the first motor are in parallel connection in the first circuit, and wherein the second motor is short cut in the second circuit.

8. The device of claim 1, further comprising a third switch in parallel connection to the second switch.

9. The device of claim 8, further comprising a fourth switch in serial connection to the third switch, wherein the series of the third and fourth switch being in parallel connection to the second switch.

10. The device of claim 1, further comprising a first power supply.

11. The device of claim 10, wherein the first electric circuit provides a first polarity of the first power supply relative to the first motor, and the second electric circuit provides a reversed second polarity of the first power supply relative to the first motor.

12. The device of claim 10, wherein the second electric circuit comprises a second power supply, which is disconnected in the first electric circuit.

13. The device of claim 1, further comprising at least two containers containing components of a dental material, and a mixer for mixing the components, the device further having a push button for operating the selector switch.

* * * * *

UNITED STATES PATENT AND TRADEMARK OFFICE
CERTIFICATE OF CORRECTION

| | |
|---|---|
| PATENT NO. | : 8,613,376 B2 |
| APPLICATION NO. | : 13/392946 |
| DATED | : December 24, 2013 |
| INVENTOR(S) | : Jens Gramann et al. |

It is certified that error appears in the above-identified patent and that said Letters Patent is hereby corrected as shown below:

In the Specification

Column 1

Line 9, delete "Brittan" and insert -- Britain --, therefor.

Columns 2-3

Lines 60-67 (Col. 2), Lines 1-3, (Col. 3), delete "The skilled....default mode." and insert the same on Col. 2, line 59, after "switches." as the continuation of the same paragraph.

Column 3

Line 42, delete "refracted" and insert -- retracted --, therefor.

Column 8

Line 33, delete "refracted" and insert -- retracted --, therefor.

Column 10

Line 28, delete "refracted" and insert -- retracted --, therefor.

Signed and Sealed this
Twelfth Day of August, 2014

Michelle K. Lee
*Deputy Director of the United States Patent and Trademark Office*